US007398277B2

United States Patent
Lin

(10) Patent No.: US 7,398,277 B2
(45) Date of Patent: Jul. 8, 2008

(54) TECHNIQUE FOR SELECTIVELY ACCESSING EVENTS WITHIN MERGED HISTORIES

(75) Inventor: Jenche Lin, Chino Hills, CA (US)

(73) Assignee: Sun Microsystems, Inc., Santa Clara, CA (US)

( * ) Notice: Subject to any disclaimer, the term of this patent is extended or adjusted under 35 U.S.C. 154(b) by 357 days.

(21) Appl. No.: 11/022,575

(22) Filed: Dec. 22, 2004

(65) Prior Publication Data

US 2006/0136492 A1    Jun. 22, 2006

(51) Int. Cl.
*G06F 17/30* (2006.01)
*G06F 7/00* (2006.01)

(52) U.S. Cl. .................... 707/101; 707/104.1
(58) Field of Classification Search ............ 707/101, 707/104.1
See application file for complete search history.

(56) References Cited

U.S. PATENT DOCUMENTS

| | | | |
|---|---|---|---|
| 6,486,895 B1 * | 11/2002 | Robertson et al. ........... 715/776 |
| 6,519,766 B1 * | 2/2003 | Barritz et al. ............... 717/130 |
| 2002/0123931 A1 * | 9/2002 | Splaver et al. .............. 705/14 |
| 2002/0188613 A1 * | 12/2002 | Chakraborty et al. ....... 707/100 |
| 2003/0064807 A1 * | 4/2003 | Walker et al. ................ 463/42 |
| 2003/0083121 A1 * | 5/2003 | Cole et al. ................... 463/16 |
| 2004/0064758 A1 * | 4/2004 | Novik et al. ................. 714/37 |
| 2004/0078451 A1 * | 4/2004 | Dietz et al. ................. 709/217 |
| 2005/0076311 A1 * | 4/2005 | Kusterer et al. ............ 715/853 |
| 2005/0091241 A1 * | 4/2005 | Mills et al. ................. 707/100 |
| 2006/0053163 A1 * | 3/2006 | Liu et al. .................. 707/104.1 |
| 2006/0080405 A1 * | 4/2006 | Gibson ....................... 709/218 |

* cited by examiner

*Primary Examiner*—Kuen S. Lu
(74) *Attorney, Agent, or Firm*—Hickman Palermo Truong & Becker LLP

(57) ABSTRACT

A method is provided for selectively accessing first and second event histories that are merged together. A graphical user interface displays events within the merged history. Access may be selectively provided to a last event immediately preceding a merge juncture within the sequential history associated with the first or the second history via the graphical user interface when the merged event is accessed. In addition or in the alternative, access may be selectively provided to the merged event via the graphical user interface when the last event associated with the first or second history is accessed. Additional interrelated methods, apparatuses, computer program products and computer systems are described.

8 Claims, 4 Drawing Sheets

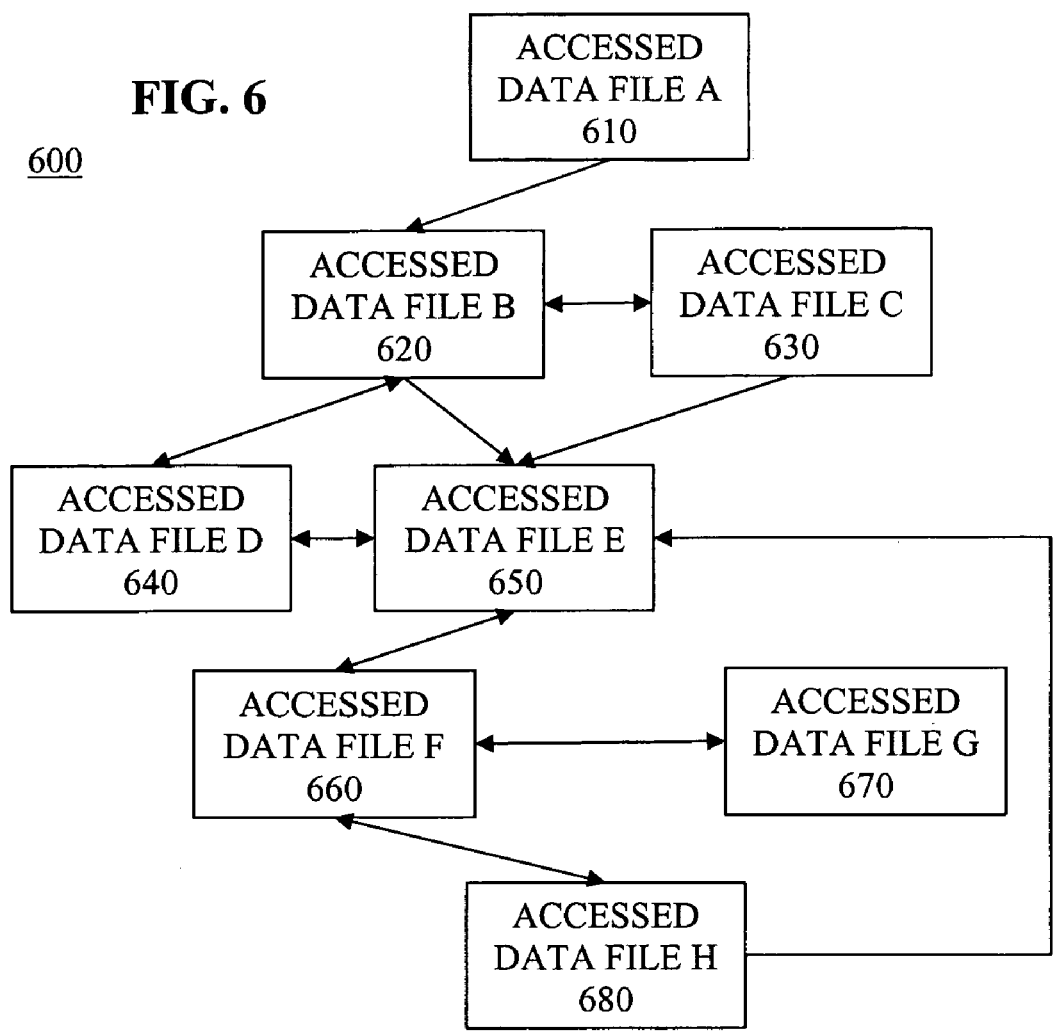

TECHNIQUE FOR SELECTIVELY ACCESSING EVENTS WITHIN MERGED HISTORIES

TECHNICAL FIELD

This invention relates to managing data.

BACKGROUND

Data files associated with transaction histories of objects are often generated by multiple data entry sources. Based on factors such as heterogeneous data entry systems, data entry error, and the like, multiple histories may be generated for a single object (rather than adding to an existing history). When separate histories are identified, they can be merged into a single set of linked data files. However, the ability to easily access the data files (e.g., the source material) associated with the merged histories is limited and/or burdensome.

With health records systems, the object may be an individual (e.g., a patient) and the data files may be associated with entries within a medical history. For example, a patient may obtain treatment at a first facility which generates or updates a first treatment record with information pertaining to the first facility treatment. When the patient subsequently obtains treatment at a second facility, the first treatment record may, for example, mistakenly not be associated with the patient and a second treatment record is then generated. At a later date, the existence of two separate treatment records is identified. These records are then merged so that all information pertaining to the patient's treatment is linked together. The point at which the documents are merged is identified within the merged histories as a merge juncture.

When viewing the data files associated with the patient on a viewer (e.g., a browser or other user interface for displaying information within the data files pertinent to a patient's medical history), a user may access one or more data files corresponding to specific events within the medical history through a table of contents (or master index), or alternatively, a user may access events in sequential (e.g., chronological) order. When accessing data files in sequential order, a graphical user interface typically provides buttons such as back, forward, first, last, and the like which indicate the next data file to be viewed. With some viewers, two sequential data files are displayed in a side-by-side fashion in order to identify the changes made between the two data files.

Conventional viewers typically only manage linear progression of events. As a result, when a merged history is accessed, a user may have problems traversing the merged history. For example, when a data file associated with a merge event is displayed and a user seeks to traverse back to a prior event, an error may result. In addition, conventional viewers do not have the ability to readily display events from all histories in a side-by-side fashion.

Furthermore, a related problem associated with conventional data file viewer systems is that they provide limited navigational functionality. Typical navigations actions that may be taken via the graphical user interface of the viewer include (i) accessing a linked document by activating a link embedded within the data file; (ii) returning to the last viewed data file by activating a back button; and (iii) accessing the last viewed data file prior to the activation of the back button by selecting a forward button. While such functionality is useful for a simple viewing of data files, with this configuration, a user does not fully appreciate the interrelationship among data files in complex systems. Therefore, additional time must be spent to identify and to access various data files that are closely associated. These efforts consume extra processing power and are inefficient.

Accordingly, it will be appreciated that there remains a need for an improved technique for providing selective access to all portions of a merged event history. It will also be appreciated that there remains a need for an improved data file viewer that identifies and provides selective access to data files that were displayed in a complete history.

SUMMARY

A method for providing access to events associated with an object is described. Such a method may include the steps of merging a first history of sequential linked events with a second history of sequential linked events to form a merged history, wherein the merged history includes a segregation of the first and second histories up to a merge juncture and a unified (with respect to the first and second histories) history of sequential linked events thereafter, the merge juncture representing a point at which the first and second histories are merged, providing a graphical user interface to display the events within the merged history, selectively providing access to a last event immediately preceding the merge juncture within the sequential history associated with the first or the second history via the graphical user interface when the merge juncture is accessed, and selectively providing access to the merge juncture via the graphical interface when the last event associated with the first or second history is accessed.

In some variations, this method omits the step of merging the first and second histories and handles histories that have already been merged. Such a variation would be applicable, for example, if the graphical user interface associated with the event histories is only used to view and make minor modifications to the histories.

In one variation, an apparatus that provides access to events associated with an object is described. Such an apparatus may include a merge unit to merge a first history of sequential linked events with a second history of sequential linked events to form a merged history, wherein the merged history includes a segregation of the first and second histories up to a merge juncture and a unified history of sequential linked events thereafter, the merge juncture representing a point at which the first and second histories are merged, an interface unit to provide a graphical user interface to display the events within the merged history, and an access unit to selectively provide access to a last event immediately preceding the merge juncture within the sequential history associated with the first or the second history via the graphical user interface when the merge juncture is accessed, and/or to selectively provide access to the merge juncture via the graphical interface when the last event associated with the first or second history is accessed.

In another variation, an apparatus is provided to access events associated with an object that are the result of merging a first history of sequential linked events with a second history of sequential linked events to form a merged history, wherein the merged history includes a segregation of the first and second histories up to a merge juncture and a unified history of sequential linked events thereafter, the merge juncture representing a point at which the first and second histories are merged. This apparatus may include an interface unit to provide a graphical user interface to display the events within the merged history, and an access unit to selectively provide access to a last event immediately preceding the merge juncture within the sequential history associated with the first or the second history via the graphical user interface when the merge juncture is accessed, and/or to selectively provide access to the merge juncture via the graphical interface when the last event associated with the first or second history is accessed.

A interrelated method for providing access to data files via a data file viewer is also described that may include the steps of updating a history list identifying each data file viewed immediately prior to the accessed data file each time a data file is accessed via the viewer, and providing a graphical user interface within the viewer to identify and selectively provide access to any of the data files within the history list from the accessed data file. In some variations, the viewer is a browser, such as an Internet browser.

An interrelated apparatus to provide access to data files via a data file viewer is also disclosed that may include an updating unit to update, each time a data file is accessed via the viewer, a history list identifying each data file viewed immediately prior to the accessed data file, and an interface unit to provide a graphical user interface within the viewer to identify and selectively provide access to any of the data files within the history list from the accessed data file.

Computer program products for implementing the steps of the described methods are also provided. Such computer program products may be embodied on computer readable material that includes executable instructions for causing a computer system to execute the one or more of the various method steps.

Computer systems having a processor, and a memory coupled to the processor are also provided. The memory may encode one or more programs that cause the processor to perform one or more of the steps of the methods described herein.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6 is a sample data file linkage schematic useful for understanding and implementing the claimed subject matter.

Like reference symbols in the various drawings indicate like elements.

DETAILED DESCRIPTION

For purposes of the current description, the term event refers to information that has been generated relating to an object (e.g., a person, a service, a product, etc.). The event may be a record and/or it may make up a data file or a portion of a data file. A history refers to a collection of events which may be collectively stored in one or more data files. The history may be a string or it may take other data forms. The events within a history may be sequentially ordered based on any criteria (e.g., in chronological order, date of entry, date of relevant event, event class, priority ranking, etc.). The term merge juncture refers to the point at which multiple histories are merged. The merge juncture may comprise a separate event within the merged history or it may be an indicator that indicates a branch for navigational purposes. Multiple histories may be merged by creating a new merged history from two or more previous histories. Alternatively, one or more histories may be merged into a pre-existing history.

Figure 1:
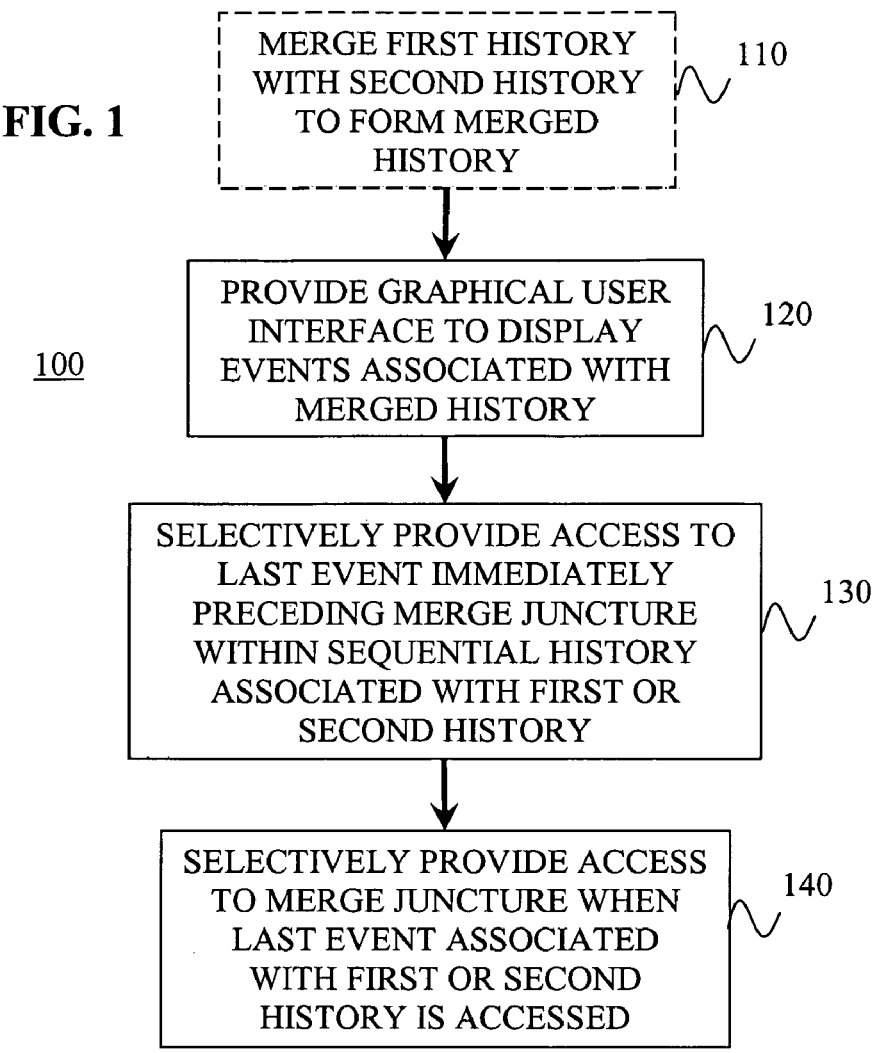
FIG. 1 is a process flow diagram of a method for providing selective access to data files of merged histories.

FIG. 1 illustrates a method 100 for providing access to events associated with an object. The events may be contained within a single data file or multiple data files and are associated. At step 110, a first history of sequential linked events is merged with a second history of sequential linked events to form a merged history. The merged history includes a segregation of or otherwise separates the first and second histories up to a merge juncture. After the merged history, a single history of sequential linked events is generated. The merge juncture represents a point at which the first and second histories are merged. Though only a single merge juncture is shown, other merge junctures in any of the first or second histories (e.g., pre-existing merge junctures) or the unified history are possible. At step 120, a graphical user interface (GUI) is provided to display the events within the merged history. At step 130, access is selectively provided to a last event immediately preceding the merge juncture within the sequential history associated with the first or the second history via the GUI when the merge juncture is accessed. At step 140, access is selectively provided to the merge juncture via the GUI when the last event associated with the first or second history is accessed. With both of the preceding steps, access may be dependent on the activation of an element within the GUI that corresponds to the desired event history progression.

The skilled artisan will recognize that step 110 may be optional depending on whether the file histories had been previously merged (which is indicated in FIG. 1 by the dashed lines). Furthermore, the skilled artisan will appreciate that one or both steps 130 and 140 may be implemented depending on the desired configuration.

Figure 2:
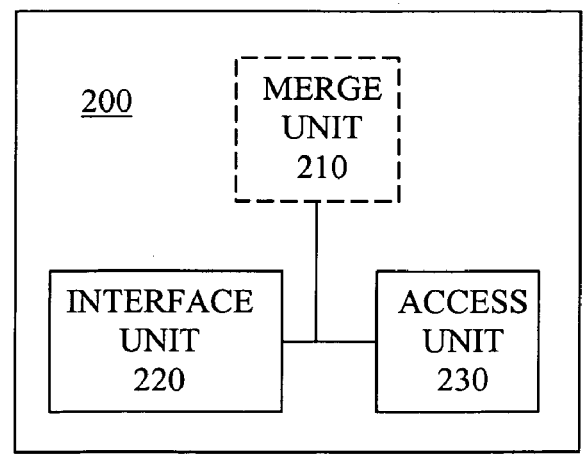
FIG. 2 is an apparatus for providing selective access to data files of merged histories.

FIG. 2 illustrates an apparatus 200 to provide access to events associated with an object. The apparatus 200 may optionally include a merge unit 210 that merges a first history of sequential linked events with a second history of sequential linked events to form a merged history (or alternatively, the apparatus 200 may be used in connection with a pre-existing merged history thereby obviating the need for the merge unit 210). The merged history includes a segregation of the first and second histories up to a merge juncture representing a point at which the first and second histories are merged and a unified history of sequential linked events after the merge juncture. The apparatus may also include an interface unit 220 that provides a graphical user interface to display the events within the merged history. The interface unit 220 may be an application that displays the contents of data files associated with various events within the merged history (e.g., an indexing application). An access unit 230 may also be included that selectively provides access to a last event immediately preceding the merge juncture within the sequential history associated with the first or the second history via the graphical user interface when the merge juncture is accessed, and/or selectively provides access to the merge juncture via the graphical interface when the last event associated with the first or second history is accessed. In one variation, the sequential history is in chronological order.

Figure 3:
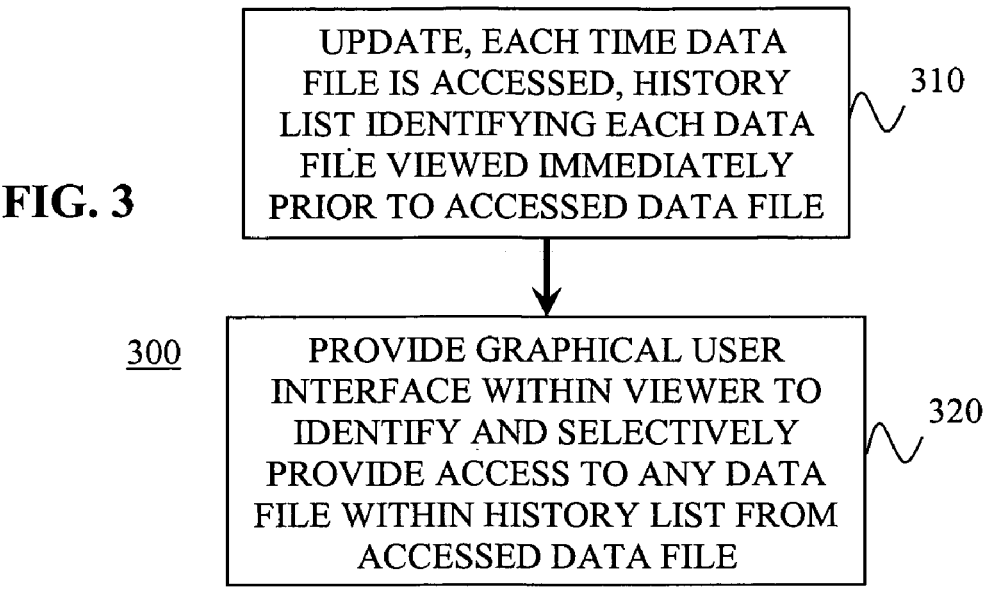
FIG. 3 is an interrelated process flow diagram of a method for selectively providing access to a data file by a viewer.

FIG. 3 illustrates a method 300 interrelated to that of FIG. 1 for providing access to data files via a data file viewer. The method 300 updates, at step 310, a history list identifying each data file viewed immediately prior to the accessed data file each time a data file is accessed via the viewer. At step 320, a graphical user interface is provided within the viewer to identify and selectively provide access to any of the data files within the history list from the accessed data file.

Figure 4:
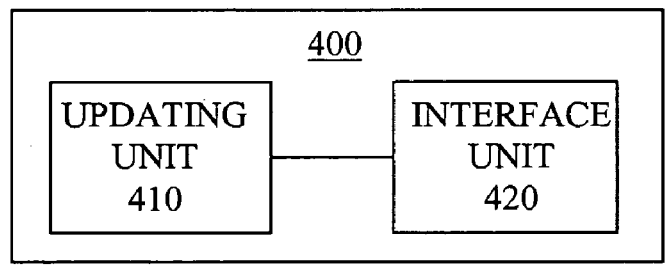
FIG. 4 is an interrelated apparatus for selectively providing access to a data file by a viewer.

FIG. 4 illustrates an apparatus 400 that provides access to data files via a data file viewer. The apparatus 400 may include an updating unit 410 that updates a history list identifying each data file viewed immediately prior to the accessed data file each time a data file is accessed via the viewer. In addition, an interface unit 420 may be included that provides a graphical user interface within the viewer to identify and selectively provide access to any of the data files within the history list from the accessed data file.

The following provides examples and optional variations useful for understanding and carrying out the above-described methods and apparatuses. These variations may be adopted singly or in combination depending on the desired and should not be construed as limiting the applicability and scope of the claimed subject matter.

Figure 5:
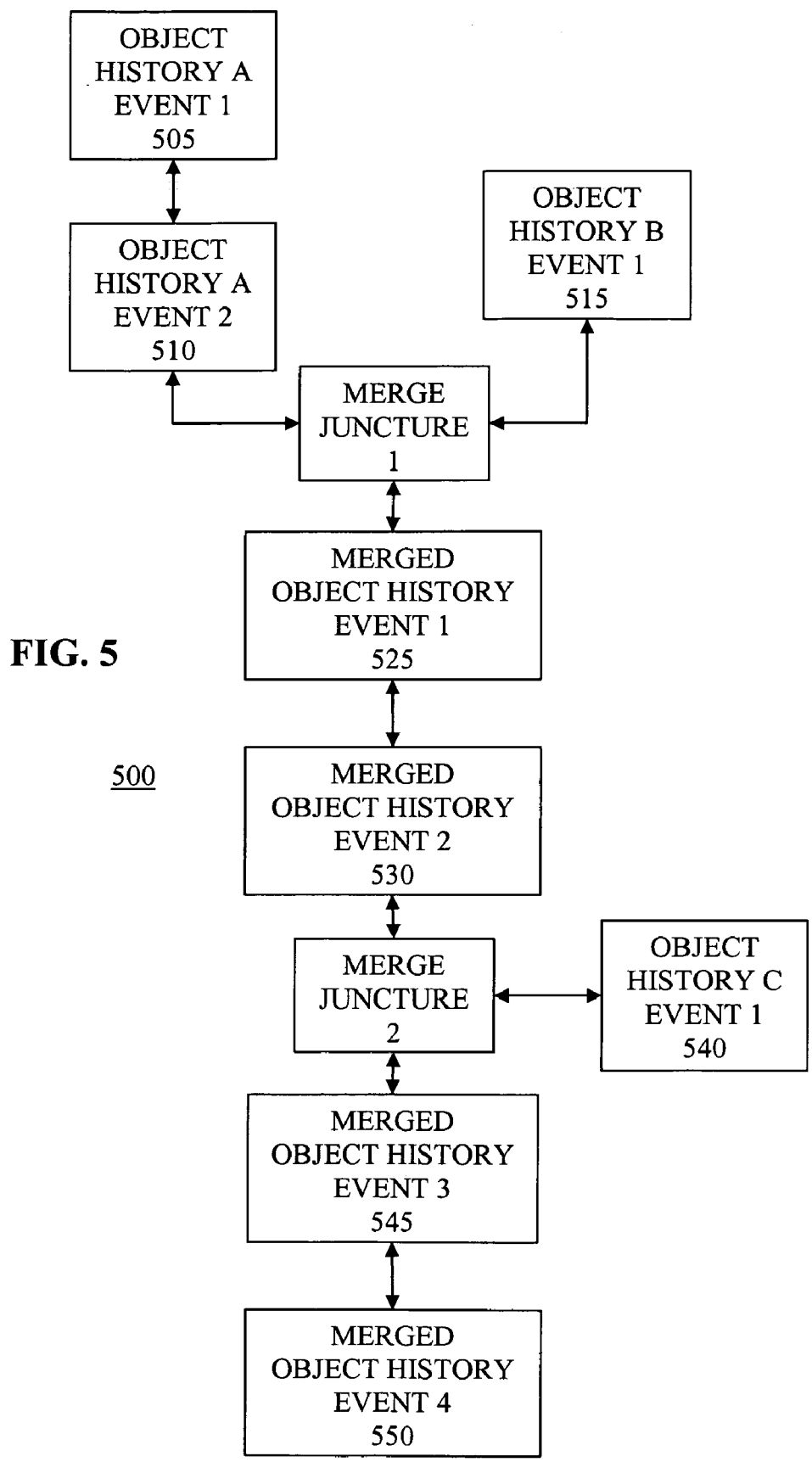
FIG. 5 is a sample merged event schematic useful for understanding and implementing the claimed subject matter.

FIG. 5 is a schematic 500 illustrating a sample merged history which contains events regarding object history A events 505, 510 and an object history B event 515 which are merged together at merge juncture 1 520. After merge juncture 1 520, two merged object history events 525, 530 occur. At this point, the merged object history is merged with yet another object history, namely object history C (having a single object history event 540) at merge juncture 2 535. Thereafter, two more merged object history events occur 545, 550.

The various events within schematic 500 may be conveyed to a user via a GUI (not shown) or alternatively via another interface with a GUI for navigation instructions. The GUI may provide various functionality for a user to access the various events 505-550 and to readily access linked events. For example, if merged object history event 4 550 is accessed, a user may either have merged object history event 3 545 displayed in a side-by-side fashion, or the user may access merged object history event 3 545 by activating an up, back, or other button.

Once merged object history event 3 545 is accessed, to travel up in the schematic, the user accesses and is notified of merge juncture 2 535 and is given the option to access either merged object history event 2 530 or object history C event 1 540. Such access may be, for example, providing a side-by-side representation of merged object history event 3 545 and object history C event 1 540. Alternatively, a user accessing a back or up button might, as a default setting, access merged object history event 2 530. With this variation, object history C event 1 540 may be accessed by selecting a button or other device which is displayed only on pages immediately succeeding a merge juncture (in a downward progression).

When a user accesses merged object history event 1 525, in order to traverse upwards or back, merged event 1 520 is accessed which results in the GUI indicating that there are two paths that may be taken, one corresponding to object history A event 2 510 and the other relating to object history B event 1 515. The GUI also provides a feature in the GUI for selecting one of these paths. Thereafter, information pertaining to the first event within the selected path (e.g., object history A event 2 510 or object history B event 1 515) is illustrated and optionally, information pertaining to merged object history event 1 525 is also illustrated.

Similarly, if a user is progressing downwards on schematic 500 from object history A event 2 510, he or she will access and be notified of merge juncture 1 520 and will be given the option of progressing down to merged object history event 1 525 or traversing upwards to object history B event 1 515. In some variations, merge juncture 1 520 and merge juncture 2 535 may be integrated into the succeeding merged object history event so that the preceding object history events prior to the merge juncture are directly linked to such object history event.

FIG. 6 is a schematic 600 that illustrates the interrelationship between multiple data files that are ordinarily linked. Such data files may be accessed via a viewer, for example, similar to Microsoft Explorer and the like (but with enhanced functionality) that displays information pertaining to data files. In some variations, the viewer is an Internet Browser and the data files web pages. Such a viewer also includes a GUI for navigating among the various data files. Unlike the example shown in FIG. 5, the data files 610-680 within FIG. 6 may be coupled together in a more complex fashion rather than in a sequential or modified parallel format. In addition, there may be numerous additional data files that are not accessed (and which are not illustrated). Any of the data files 610-680 may be coupled to any of the other data files 610-680.

The linkages illustrated in FIG. 6 show a sample navigation path taken by a user. The user may first access accessed data file A 610 whereby he or she traverses to data file B 620. During the course of a session (or other defined time period), the user accesses the remaining illustrated linked data files, some of them on more than one occasion. These files may be accessed through the activation of embedded links within the data file (e.g., the traversal from accessed data file D 640 to accessed data file E 650) or alternatively, a user may enter in an identifier associated with a data file to directly access such data file (e.g., the traversal from accessed data file H 680 to accessed data filed E 650) Unlike conventional viewers that only allow a user to go back or forward to activate links embedded, the GUI of the current viewer will allow a user to traverse to any other data files that were accessed immediately prior to the current data file.

For example, if a user has progressed from accessed data file F 660 to accessed data file E 650, the user is provided the option, via a GUI, to access each of accessed data file B 620, accessed data file C 630, accessed data file D 640, and accessed data file H 650. The GUI may provide separate activation devices for each of these various paths (e.g., buttons) or it may include a multi-step process under which a first device is activated which displays a list of all previously linked data files. Thereafter, a link or device associated with one of the listed data files is activated in order to traverse away from the current data file.

In some variations, the accessed data files A-H 610-680 in FIG. 6 may be web pages which are accessible via a browser. Rather than conventional techniques in which a back button returns a user to the previously viewed page, a button or other device will be provided in the browser graphical user interface that identifies and allows a user to access one or more of the following (i) all pages that were accessed after each time the current page was accessed; (ii) all pages that were accessed prior to each time the current page was accessed; (iii) all pages that were accessed after each time the current page was accessed and all pages that were accessed prior to each time the current page was accessed; and/or (iv) a portion of any of the preceding. In other words, the browser identifies related web pages and allows the traversal to any of such pages. The related web pages may be preceding web pages, succeeding web pages, or a combination of both. Certain recently accessed web pages (e.g., the last immediately accessed web page) may be excluded in some variations depending on the desired implementation.

The skilled artisan will appreciate that there are many advantages associated with the subject matter described herein. When merged event histories are being examined, a user may readily examine and compare files from various event histories regardless of whether the events were merged into the current history or otherwise. In addition, the techniques described herein also allow a user to more conveniently access data files that are linked to a plurality of other accessed data files.

The subject matter described herein may be implemented in digital electronic circuitry, or in computer hardware, firmware, software, or in combinations of them. Apparatus of the subject matter described herein may be implemented in a computer program product tangibly embodied in an information carrier, e.g., in a machine-readable storage device or in a propagated signal, for execution by a programmable processor; and method steps of the subject matter described herein may be performed by a programmable processor executing a program of instructions to perform functions of the subject matter described herein by operating on input data and generating output. The subject matter described herein may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language, including compiled or interpreted languages, and it may be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, ASICs (application-specific integrated circuits).

A number of embodiments of the invention have been described. Nevertheless, it will be understood that various modifications may be made without departing from the scope of the invention. Accordingly, other embodiments are within the scope of the following claims.

What is claimed is:

1. A method for providing access to events associated with an object, the method comprising the steps of:
   merging a first history of sequential linked events with a second history of sequential linked events to form a merged history, wherein the merged history includes a segregation of the first and second histories up to a merge juncture and a unified history of sequential linked events thereafter, the merge juncture representing a point at which the first and second histories are merged;
   providing a graphical user interface to display the events within the merged history;
   allowing a user to access the merge juncture;
   when the merge juncture is accessed, providing the user, via the graphical user interface, an option of accessing an event in the first history that immediately precedes the merge juncture or an event in the second history that immediately precedes the merge juncture; and
   selectively providing access to the merge juncture via the graphical interface when the last event associated with the first or second history is accessed.

2. A method for providing access to events associated with an object that are the result of merging a first history of sequential linked events with a second history of sequential linked events to form a merged history, wherein the merged history includes a segregation of the first and second histories up to a merge juncture and a unified history of sequential linked events thereafter, the merge juncture representing a point at which the first and second histories are merged, the method comprising the steps of:
   providing a graphical user interface to display the events within the merged history;
   allowing a user to access the merge juncture;
   when the merge juncture is accessed, providing the user, via the graphical user interface, an option of accessing an event in the first history that immediately precedes the merge juncture or an event in the second history that immediately precedes the merge juncture; and
   selectively providing access to the merge juncture via the graphical interface when the last event associated with the first or second history is accessed.

3. An apparatus to provide access to events associated with an object, the apparatus comprising:
   a merge unit to merge a first history of sequential linked events with a second history of sequential linked events to form a merged history, wherein the merged history includes a segregation of the first and second histories up to a merge juncture and a unified history of sequential linked events thereafter, the merge juncture representing a point at which the first and second histories are merged;
   an interface unit to provide a graphical user interface to display the events within the merged history; and
   an access unit, the access unit allowing a user to access the merge juncture, and when the merge juncture is accessed, the access unit providing the user, via the graphical user interface, an option of accessing an event in the first history that immediately precedes the merge juncture or an event in the second history that immediately precedes the merge juncture, the access unit further selectively providing access to the merge juncture via the graphical interface when the last event associated with the first or second history is accessed.

4. An apparatus to provide access to events associated with an object that are the result of merging a first history of sequential linked events with a second history of sequential linked events to form a merged history, wherein the merged history includes a segregation of the first and second histories up to a merge juncture and a unified history of sequential linked events thereafter, the merge juncture representing a point at which the first and second histories are merged, the apparatus comprising:

an interface unit to provide a graphical user interface to display the events within the merged history; and an access unit, the access unit allowing a user to access the merge juncture, and when the merge juncture is accessed, the access unit providing the user, via the graphical user interface, an option of accessing an event in the first history that immediately precedes the merge juncture or an event in the second history that immediately precedes the merge juncture, the access unit further selectively providing access to the merge juncture via the graphical interface when the last event associated with the first or second history is accessed.

5. A computer program product for providing access to events associated with an object, embodied on a computer readable storage medium, that includes executable instructions for causing a computer system to:

merge a first history of sequential linked events with a second history of sequential linked events to form a merged history, wherein the merged history includes a segregation of the first and second histories up to a merge juncture and a unified history of sequential linked events thereafter, the merge juncture representing a point at which the first and second histories are merged;

provide a graphical user interface to display the events within the merged history;

allow a user to access the merge juncture;

when the merge juncture is accessed, provide the user, via the graphical user interface, an option of accessing an event in the first history that immediately precedes the merge juncture or an event in the second history that immediately precedes the merge juncture; and selectively provide access to the merge juncture via the graphical interface when the last event associated with the first or second history is accessed.

6. A computer program product for providing access to events associated with an object that are the result of merging a first history of sequential linked events with a second history of sequential linked events to form a merged history, wherein the merged history includes a segregation of the first and second histories up to a merge juncture and a unified history of sequential linked events thereafter, the merge juncture representing a point at which the first and second histories are merged, the computer program product being embodied on a computer readable storage medium and including executable instructions for causing a computer system to:

provide a graphical user interface to display the events within the merged history;

allow a user to access the merge juncture;

when the merge juncture is accessed, provide the user, via the graphical user interface, an option of accessing an event in the first history that immediately precedes the merge juncture or an event in the second history that immediately precedes the merge juncture; and selectively provide access to the merge juncture via the graphical interface when the last event associated with the first or second history is accessed.

7. A computer system comprising: a processor; and a memory coupled to the processor, the memory encoding one or more programs, the one or more programs causing the processor to perform a method for providing access to events associated with an object according to the steps of:

merging a first history of sequential linked events with a second history of sequential linked events to form a merged history, wherein the merged history includes a segregation of the first and second histories up to a merge juncture and a unified history of sequential linked events thereafter, the merge juncture representing a point at which the first and second histories are merged;

providing a graphical user interface to display the events within the merged history;

allowing a user to access the merge juncture;

when the merge juncture is accessed, providing the user, via the graphical user interface, an option of accessing an event in the first history that immediately precedes the merge juncture or an event in the second history that immediately precedes the merge juncture; and selectively providing access to the merge juncture via the graphical interface when the last event associated with the first or second history is accessed.

8. A computer system comprising: a processor; and a memory coupled to the processor, the memory encoding one or more programs, the one or more programs causing the processor to perform a method for providing access to events associated with an object that are the result of merging a first history of sequential linked events with a second history of sequential linked events to form a merged history, wherein the merged history includes a segregation of the first and second histories up to a merge juncture and a unified history of sequential linked events thereafter, the merge juncture representing a point at which the first and second histories are merged, the method performed according to the steps of:

providing a graphical user interface to display the events within the merged history;

allowing a user to access the merge juncture;

when the merge juncture is accessed, providing the user, via the graphical user interface, an option of accessing an event in the first history that immediately precedes the merge juncture or an event in the second history that immediately precedes the merge juncture; and selectively providing access to the merge juncture via the graphical interface when the last event associated with the first or second history is accessed.

* * * * *